United States Patent
Esarey et al.

(10) Patent No.: US 11,306,946 B2
(45) Date of Patent: Apr. 19, 2022

(54) AIR-ACTIVATED DEVICE-WARMING SYSTEMS AND METHODS

(71) Applicant: Ignik Outdoors, Inc., Bainbridge Island, WA (US)

(72) Inventors: Graeme Esarey, Bainbridge Island, WA (US); Scott Comins, Seattle, WA (US); Peter Pontano, Seattle, WA (US)

(73) Assignee: Ignik Outdoors, Inc., Bainbridge Island, WA (US)

( * ) Notice: Subject to any disclaimer, the term of this patent is extended or adjusted under 35 U.S.C. 154(b) by 0 days.

(21) Appl. No.: 16/669,308

(22) Filed: Oct. 30, 2019

(65) Prior Publication Data
US 2021/0131704 A1 May 6, 2021

(51) Int. Cl.
*F24V 30/00* (2018.01)
*H05K 7/20* (2006.01)

(52) U.S. Cl.
CPC ........... *F24V 30/00* (2018.05); *H05K 7/2039* (2013.01)

(58) Field of Classification Search
CPC ........................................................ F24V 30/00
See application file for complete search history.

(56) References Cited

U.S. PATENT DOCUMENTS

| | | | |
|---|---|---|---|
| 5,809,573 A | 9/1998 | Bary | |
| 9,528,780 B2 | 12/2016 | Wray et al. | |
| 9,668,913 B2 | 6/2017 | Matsuo | |
| 9,821,204 B2 | 11/2017 | Wolfe et al. | |
| 9,920,954 B2 | 3/2018 | Nishioka et al. | |
| 10,010,121 B2 | 7/2018 | Kumprey et al. | |
| 10,104,974 B1 | 10/2018 | Baureis | |
| 2015/0232254 A1* | 8/2015 | Hutter | B65D 65/14 206/484.2 |
| 2020/0046550 A1* | 2/2020 | Igaue | A61F 7/034 |
| 2021/0137727 A1* | 5/2021 | Laubach | B32B 27/40 |

\* cited by examiner

*Primary Examiner* — Jason Lau
(74) *Attorney, Agent, or Firm* — Æon Law; Adam L. K. Philipp; Jonathan E. Olson

(57) ABSTRACT

Methods and systems are presented for configuring oxygen barriers for controlled access to chemical warming agents such as wood fiber, vermiculite, activated charcoal, iron, and salt. In this way a smart phone, syringe, or other cold-sensitive device may be warmed by such agents to restore or maintain functionality in a frigid environment.

19 Claims, 4 Drawing Sheets

Fig. 5

AIR-ACTIVATED DEVICE-WARMING SYSTEMS AND METHODS

DETAILED DESCRIPTION

The detailed description that follows is represented largely in terms of processes and symbolic representations of operations by conventional computer components, including a processor, memory storage devices for the processor, connected display devices and input devices. Furthermore, some of these processes and operations may utilize conventional computer components in a heterogeneous distributed computing environment, including remote file servers, computer servers and memory storage devices.

The phrases "in one embodiment," "in various embodiments," "in some embodiments," and the like are used repeatedly. Such phrases do not necessarily refer to the same embodiment. The terms "comprising," "having," and "including" are synonymous, unless the context dictates otherwise. As used herein a quantity is "about" a value X only if they differ by less than a factor of 3, unless context dictates otherwise. As used herein "numerous" means hundreds or more, unless context dictates otherwise. As used herein a structure is "porous" only if it has numerous moisture-permeable pores (i.e. holes smaller than 5 microns in diameter) pervading therethrough. As used herein a structure is "absorbent" only if it is porous enough to soak up more than 5 microliters of liquid per hour by wicking (capillary action, e.g.).

"Activated," "additional," "adhesive," "adjacent," "aggregated," "airtight," "alternative," "as," "assembled," "at least," "basically," "between," "by," "chemical," "closable," "cold-sensitive," "combustible," "comprising," "configured," "consisting," "contained," "corresponding," "cost-effective," "created," "cross-sectional," "differing," "distal," "effective," "emitted," "essentially," "established," "first," "frigid," "having," "herein," "inactive," "including," "increased," "initial," "limited," "maintaining," "manual," "median," "modified," "more," "nominal," "of," "opened," "organic," "other," "overall," "oxygen-rich," "partial," "per second," "positioned," "prescribed," "reflective," "removed," "restickable," "second," "single-piece," "skilled," "so as," "such," "swiftly," "thereafter," "thereby," "triggered," "upon," "warming," "wherein," "within," or other such descriptors herein are used in their normal yes-or-no sense, not merely as terms of degree, unless context dictates otherwise. In light of the present disclosure those skilled in the art will understand from context what is meant by "distal" and by other such positional descriptors used herein.

As used herein one value is "on the order" of another if the two values are within an order of magnitude (i.e. if they differ by less than a factor of ten).

Reference is now made in detail to the description of the embodiments as illustrated in the drawings. While embodiments are described in connection with the drawings and related descriptions, there is no intent to limit the scope to the embodiments disclosed herein. On the contrary, the intent is to cover all alternatives, modifications and equivalents. In alternate embodiments, additional devices, or combinations of illustrated devices, may be added to, or combined, without limiting the scope to the embodiments disclosed herein.

Figure 1:
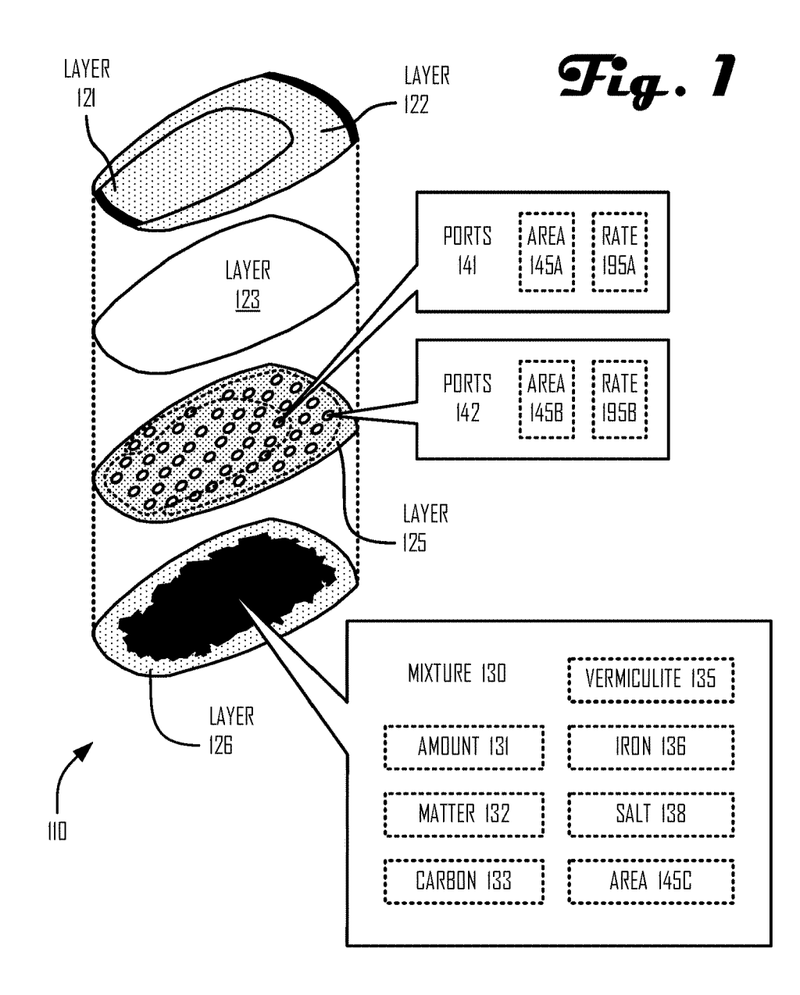
FIG. 1 illustrates an exploded view of an air-activated warming assembly according to one or more embodiments.
Figure 2:
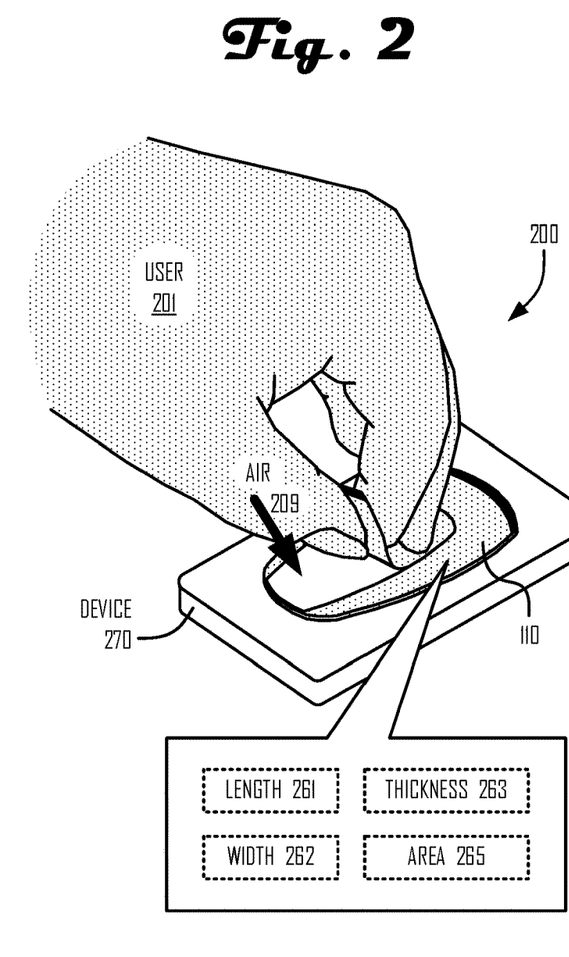
FIG. 2 illustrates a system including the assembly of FIG. 1 by which a user can operate an assembly so as to choose between distinct rates of heat emission according to one or more embodiments.

FIG. 1 illustrates an exploded view of an assembly 110 configured to house one or more (instances of) air-activated chemical warming mixtures 130. Side-by-side layers 121, 122 may be selectively removed by peeling them away as shown in FIG. 2. After either or both such removals, a mesh layer 123 allows substantially unobstructed air ingress through multiple ports 141, 142 (of an infrared-reflective layer 125, e.g.) as shown to the air-activated chemical warming mixture(s) 130. Because other avenues of air ingress (through layer 126, e.g.) are blocked/airtight, the effective (cross-sectional) area 145A of such ports 141 basically limits the rate of oxygen ingress and thereby controls the rate 195A of heat emission (in calories per second, e.g.). By choosing whether or when to remove layer 122 as well, a user can effectively increase a cross-sectional ingress area 145B by the addition of several additional ports 142. This relaxes the limited overall rate of oxygen ingress and thereby increases the rate 195B of heat emission (in calories per second, e.g.) by more than 10%.

Such mixtures 130 may include various amounts 131 of combustible organic matter 132 (dry wood fiber, e.g.), of activated carbon 133, of vermiculite 135, of iron 136, of salt 138, of other fillers or reactants, or of combinations of these. Such mixtures 130 may primarily comprise fine particles (powders, e.g.) having an aggregate surface area 145C much larger than the above-described port-limited (effective) areas 145A-B.

As used herein a flow is an "ingress" if it is primarily directed toward one or more chemical warming agents (by diffusion or convection, e.g.). As used herein an "oxygen barrier" includes an oxygen-impermeable layer or a layer semi-permeable to oxygen with pores small enough to slow diffusion flow therethrough by more than 50%.

Referring now to FIG. 2, there is shown a system 200 that allows a user 201 to operate assembly 110 so as to choose among (an airtight inactive mode and respective active modes featuring) distinct rates 195A-B of heat emission. To invoke a "medium" rate 195A, user 201 opens a first oxygen barrier by removing a single-piece first layer 121 (as shown), allowing a medium amount of oxygen-rich air 209 to flow, or at least allowing oxygen therein to flow, through ports 141 to mixture 130. To invoke a "high" rate 195B, user 201 thereafter opens a second oxygen barrier by removing another single-piece layer 122 as shown, allowing a medium amount of oxygen-rich air to flow, or at least allowing oxygen therein to flow, through ports 142 to mixture 130.

This can occur, for example, in a context in which the assembly 110 has a length 261 of 70 to 170 millimeters (mm), a width 262 of 10 to 90 mm, a thickness of 0.2 to 2 mm, a mass of 10 to 90 grams, a footprint area 265 within an order of magnitude of 500 square millimeters, and a footprint with rounded corners (so that assembly 110 can serve well as a hand warmer inside of a glove as well, e.g.). In some variants, for example, an annular periphery (having a median width) narrower than 8 mm may be sealed (laminated, e.g.) to facilitate cost-effective manufacture. Alternatively or additionally, some or all of the layers 121, 122, 123, 125, 126 as shown may be made of biodegradable materials.

Figure 3:
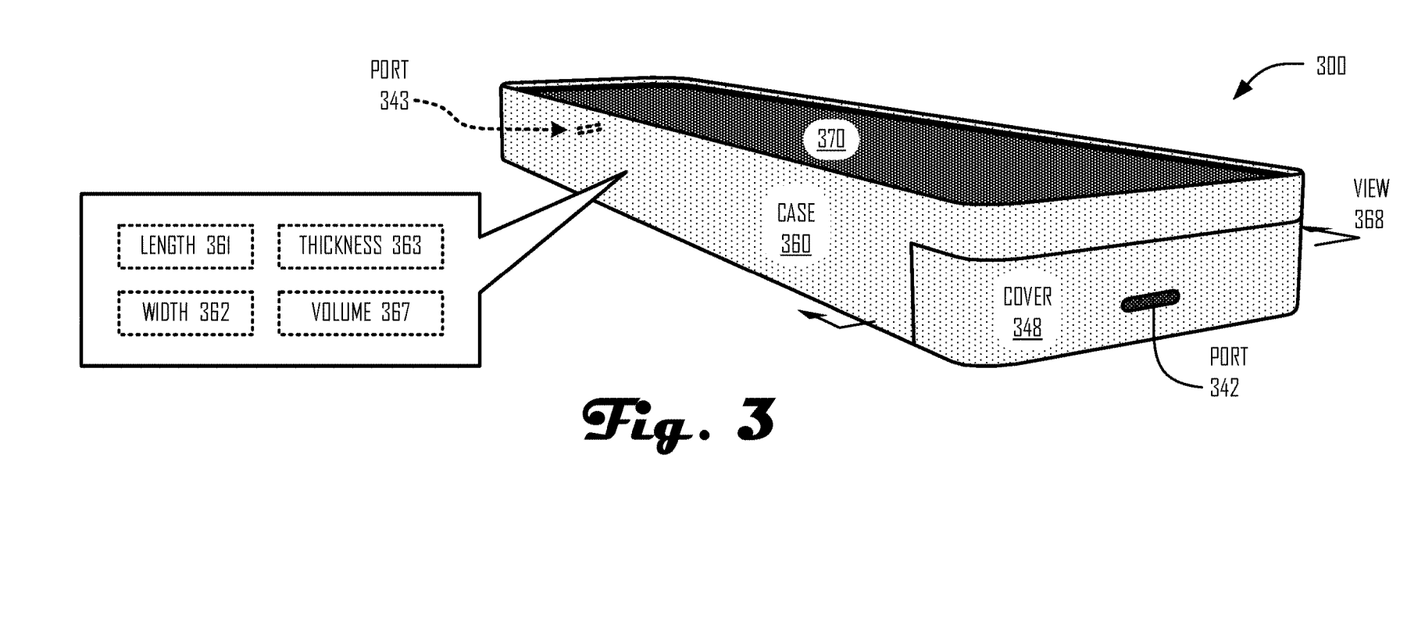
FIG. 3 illustrates a system in which a mobile device case facilitates air-activated warming according to one or more embodiments.

Referring now to FIG. 3, there is shown a system 300 that optionally implements one or more features of system 200. A case 360 is provided with a length 361 and width 362 that is conventional for protecting a smartphone or similar mobile device 370. Case 360 has an atypically large thickness 363, however, to accommodate frigid temperatures that would otherwise damage device 370 or render it inoperative (or both). This can occur, for example, in a context in which case 360 (with device 370 and cover 348) provides an air exclusion structure within which one or more chemical warming agents can be given limited access to air 209 therein so that a controlled quantity of initial heat energy (limited by an air volume 367 therein) can be released, in which the cold-sensitive device is rendered operative in a frigid environment by that controlled quantity of heat, in which that controlled quantity is not enough to damage the device 370, and in which a trickle of oxygen (through one or more ports 342, 343, e.g.) thereafter maintains the device 370 at a suitable temperature over a period of days or weeks. Although the calibration of such controlled quantities will depend upon the particular design, in light of teachings herein, some such experimentation is not undue. See also FIG. 4, which depicts a cross-sectional view 368 of device 370 and case 360.

Figure 4:
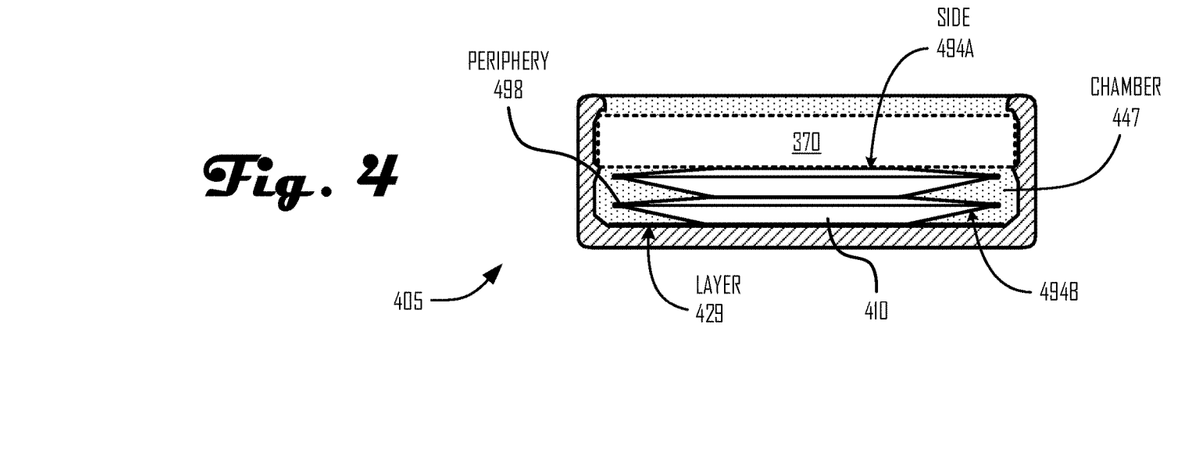
FIG. 4 illustrates a cross-sectional view of the system of FIG. 3 according to one or more embodiments.

Referring now to FIG. 4, there is shown a containment 405 that is large enough for one or more warming-agent-containment assemblies 410 in one or more chambers 447 having a limited (initial) air volume 367 of 10-100 milliliters. After consuming most of the oxygen inside chamber 447 as shown, for example, warming agents inside the one or more assemblies 410 may obtain additional oxygen primarily through one or more ports 342,343 having an aggregate (effective) oxygen ingress area (as area 145B, e.g.) on the order of 2 square millimeters. In some variants a distal side 494B of an assembly 110 may include an infrared-reflective layer 125 decreasing a fraction of heat energy wasted (on heating the case 360 rather than the device 370, e.g.). In others another portion of an exclusion structure (case 360, e.g.) may support or otherwise include an infrared-reflective coating or other layer 429. Alternatively or additionally, some assemblies 410 may be assembled with an annular periphery 498 configured (laminated, e.g.) so that a primary side 494A of an assembly 110, 410 (has a surface area 265 that) is more than 1% smaller than that of a distal side 494B thereof and thereby further to enhance heat transfer to the device 270, 370.

Figure 5:
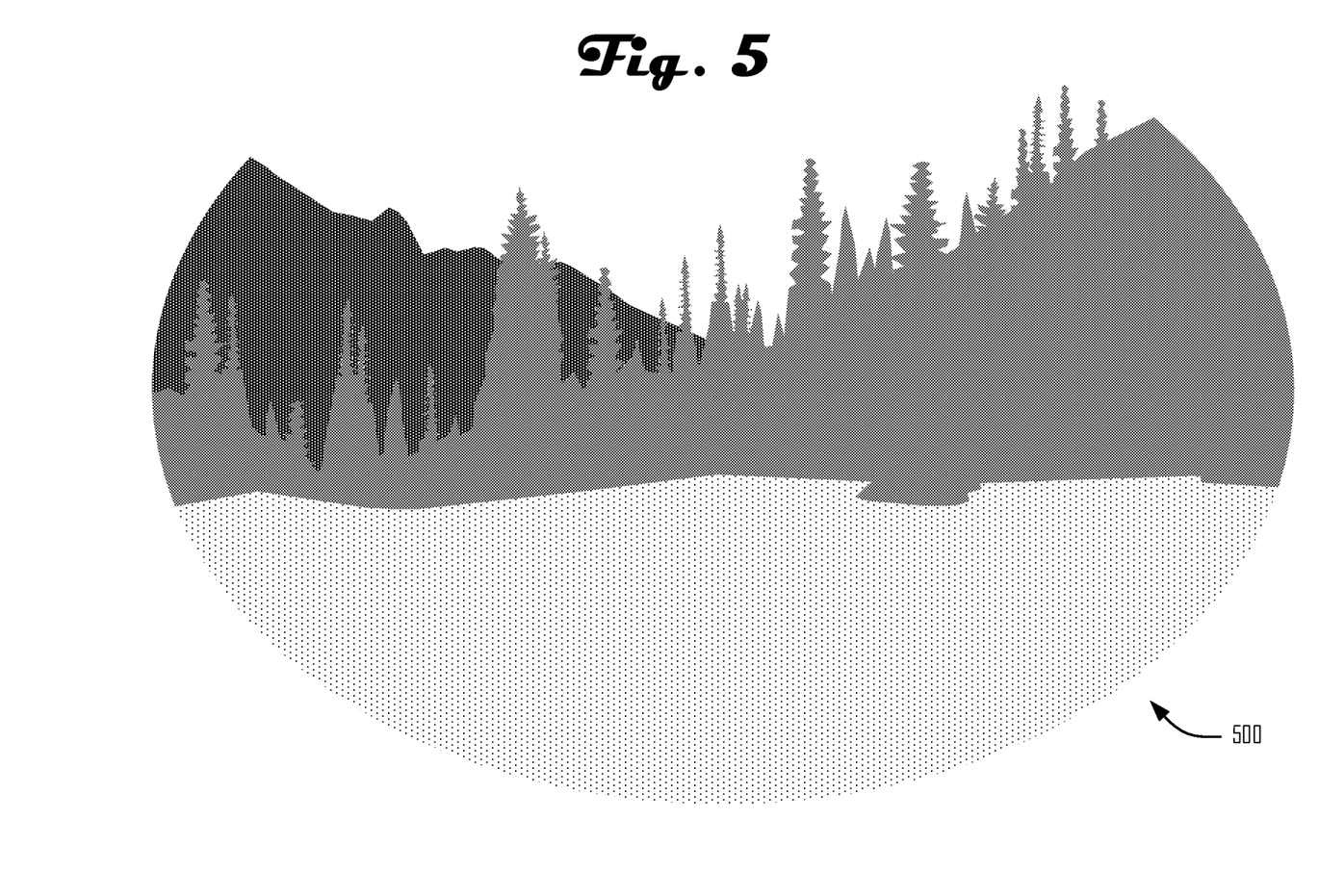
FIG. 5 illustrates a frigid environment in which one or more variant embodiments may be especially useful.

Referring now to FIG. 5, there is shown a frigid environment 500 in which a functionality of a smartphone, inhaler, syringe, or other device 270, 370 may become impaired because of excessive cold. As used herein, a "frigid" environment is at or below zero Celsius. As used herein a device is "cold-sensitive" if one or more functional components thereof is at risk of changing form (e.g. freezing), being damaged, or otherwise not functioning because of a temperature thereof becoming too low. Ordinary gloves and blankets are not "cold-sensitive" devices as described herein, although their utility (e.g. comfort) may be incrementally enhanced by warming in some contexts.

Figure 6:
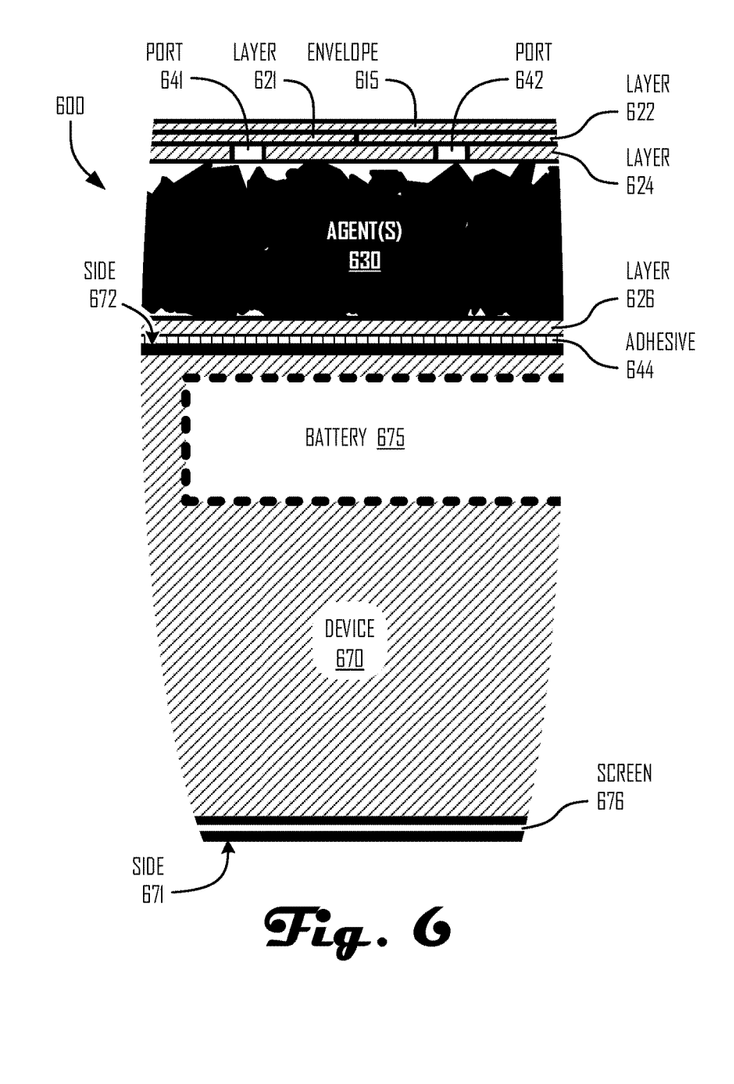
FIG. 6 illustrates another cross-sectional view of an air-activated warming system according to one or more variant embodiments.

Referring now to FIG. 6, there is shown a system 600 that optionally implements one or more features of the above-described systems 200, 300. One or more chemical warming agents 630 (as exemplified in FIG. 1, e.g.) are configured among layers 621, 622, 624, 626 in an assembly 110, 410 such as those described above. An oxygen barrier (including an airtight layer 621, e.g.) of a first exclusion structure (such as a sealed envelope 615 or similar containment 405, e.g.) is opened (by a user 201 removing layer 621, e.g.). This establishes an oxygen ingress area (as area 145A, e.g.) of the one or more chemical warming agents 630 that is quite small in comparison to a surface area 145C thereof, wherein the ingress area effectively limits a rate 195A of heat emission. Another oxygen barrier (a cover 348 or other closable structure, e.g.) of a second exclusion structure (including an airtight layer 622, e.g.) is also configured to be opened—selectively—if the user 201 wants faster heat emission (at rate 195B, e.g.). The ports 641, 642 that are opened by these respective actions are at least as shown. In some contexts the assembly may be affixed by (an adhesive 644 or one or more other) positioning elements to a back side 672 of an electronic device 670 so as to warm an adjacent internal component of the device 670 (a battery 675, e.g.). Alternatively or additionally one or more assemblies 110, 410 may likewise be positioned so as to warm an adjacent component on the front side 671 of the device 670 (a display screen 676, e.g.). This can occur, for example, in a context in which such assemblies 110, 410 are provided with suitable directions to ensure that excessive heat does not damage the device 670 or create a hazardous situation.

Figure 7:
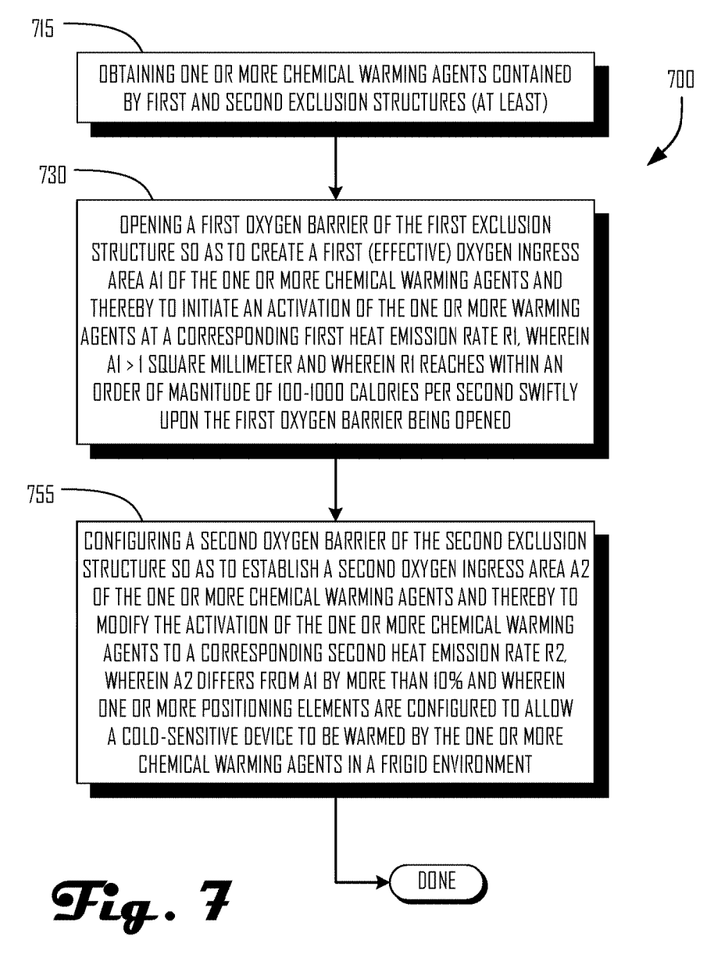
FIG. 7 illustrates a flow chart of operations relating to air-activated warming system according to one or more variant embodiments.

Referring now to FIG. 6, there is shown task flow 700 in light of one or more technologies herein. Operation 715 describes obtaining one or more chemical warming agents contained by first and second exclusion structures (e.g. one or more users 201 buying or constructing an assembly 110, 410 containing such agents).

Operation 730 describes opening a first oxygen barrier of the first exclusion structure so as to create a first oxygen ingress area A1 of the one or more chemical warming agents and thereby to initiate an activation of the one or more warming agents at a corresponding first heat emission rate R1 (e.g. one or more users 201 opening a first oxygen barrier (an airtight layer 121, 621, e.g.) of a first exclusion structure (a sealed envelope or similar containment 405, e.g.) so as to establish a first oxygen ingress area A1 (as area 145A, e.g.) of the one or more chemical warming agents 630 and thereby to initiate an activation of the one or more chemical warming agents 630 at a corresponding first heat emission rate R1). This can occur, for example, in a context in which A1>1 square millimeter, in which heat emission rate R1 reaches within an order of magnitude of 100-1000 calories per second swiftly upon the first oxygen barrier being opened, and in which the first heat emission rate R1 is an omnidirectional, overall emission value. Alternatively or additionally, the "heat emission rates" described herein may pertain to emissions from the one or more chemical warming agents 630 to a device they are configured to warm (e.g. by adjacent placement during an activated emission).

Operation 755 describes configuring a second oxygen barrier of the second exclusion structure so as to establish a second oxygen ingress area A2 of the one or more chemical warming agents and thereby to modify the activation of the one or more chemical warming agents to a corresponding second heat emission rate R2 (e.g. one or more users configuring a second oxygen barrier (another layer 122 or openable port 342, e.g.) of a second exclusion structure (a layer 125 or other container, e.g.) so as to establish a second oxygen ingress area A2 (as area 145B, e.g.) of the one or more chemical warming agents 630 and thereby to modify the activation of the one or more chemical warming agents 630 to a corresponding second heat emission rate R2 (as rate 195B, e.g.). This can occur, for example, in a context in which the second oxygen ingress area A2 differs significantly from the first oxygen ingress area A1 so as to allow a smartphone, syringe, respirator, or other cold-sensitive device 270, 370, 670 to be warmed by the one or more chemical warming agents 630, in which multiple types of chemical warming devices would otherwise be necessary to accommodate the users' inability to adapt a given assembly 110, 410 for a particular use in the field.

In light of teachings herein, numerous existing techniques may be applied for configuring special-purpose warming structures and materials as described herein without undue experimentation. See, e.g., U.S. Pat. No. 10,010,121 ("Hand warmer with a sealable end"); U.S. Pat. No. 10,104,974 ("Device and method for warming a seat"); U.S. Pat. No. 9,920,954 ("Heating tool"); U.S. Pat. No. 9,821,204 ("Heated lacrosse stick shaft"); U.S. Pat. No. 9,668,913 ("Biodegradable disposable hand warmer"); U.S. Pat. No. 9,528,780 ("Methods, devices and systems for extraction of thermal energy from a heat conducting metal conduit"); and U.S. Pat. No. 5,809,573 ("Exothermic chemically heated ear warmer"). These documents are incorporated herein by reference to the extent not inconsistent herewith.

With respect to the numbered clauses and claims expressed below, those skilled in the art will appreciate that recited operations therein may generally be performed in any order. Also, although various operational flows are presented in a sequence(s), it should be understood that the various operations may be performed in other orders than those which are illustrated or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise. Also in the numbered clauses below, specific combinations of aspects and embodiments are articulated in a shorthand form such that (1) according to respective embodiments, for each instance in which a "component" or other such identifiers appear to be introduced (with "a" or "an," e.g.) more than once in a given chain of clauses, such designations may either identify the same entity or distinct entities; and (2) what might be called "dependent" clauses below may or may not incorporate, in respective embodiments, the features of "independent" clauses to which they refer or other features described above.

CLAUSES 1. (Independent) An air-activated device warming method, comprising:

obtaining one or more chemical warming agents 630 (having within an order of magnitude of 35 grams of a mixture 130 in proximity of a handheld device, e.g.);

opening a first oxygen barrier (an airtight layer 121, 621, e.g.) of a first exclusion structure (an airtight cellophane envelope 615 or the like, e.g.) so as to establish a (containment 405 including one or more openable ports 621 or otherwise having an aggregate or other nominal) first oxygen ingress area A1 (as area 145A, e.g.) of the one or more chemical warming agents 630 and thereby to initiate an activation of the one or more chemical warming agents 630 at a corresponding first heat emission rate R1, wherein A1>1 square millimeter and wherein R1 reaches within an order of magnitude of 100-1000 calories per second upon the first oxygen barrier being opened; and configuring a second oxygen barrier (another layer 122 or openable port 342, e.g.) of a second exclusion structure (a layer 125 or other container, e.g.) so as to establish a (total or other nominal) second oxygen ingress area A2 (as area 145B, e.g.) of the one or more chemical warming agents 630 and thereby to modify the activation of the one or more chemical warming agents 630 to a corresponding second heat emission rate R2 (as rate 195B, e.g.), wherein the second oxygen ingress area A2 differs from the first oxygen ingress area A1 by more than 1%.

2. The method of any of the above METHOD CLAUSES, wherein the first and second heat emission rates R1 and R2 pertain only to that portion of heat emitted by the one or more chemical warming agents 630 to a device 270, 370, 670 that the one or more chemical warming agents 630 are configured to warm.

3. The method of any of the above METHOD CLAUSES, comprising:

placing (at least) the one or more chemical warming agents 630 within an enclosure (e.g. a case, glove, tent, or bag) to be warmed.

4. The method of any of the above METHOD CLAUSES, comprising:

placing the one or more chemical warming agents 630 and the second exclusion structure within an enclosure or other device to be warmed.

5. The method of any of the above METHOD CLAUSES, wherein the configuring the second oxygen barrier causes a (smartphone, syringe, or other) cold-sensitive device 270, 370, 670 to be warmed by the one or more chemical warming agents 630.

6. The method of any of the above METHOD CLAUSES, wherein R1 reaches within an order of magnitude of 100 calories per second upon the first oxygen barrier being opened.

7. The method of any of the above METHOD CLAUSES, wherein R1 reaches within an order of magnitude of 1000 calories per second upon the first oxygen barrier being opened.

8. The method of any of the above METHOD CLAUSES, wherein the second exclusion structure at least partly comprises a phone case 360.

9. The method of any of the above METHOD CLAUSES, wherein the second exclusion structure at least partly comprises a removable cover 348.

10. The method of any of the above METHOD CLAUSES, wherein the second exclusion structure at least partly comprises a replaceable cover 348.

11. The method of any of the above METHOD CLAUSES, wherein the opening the first oxygen barrier of the first exclusion structure essentially consists of:

maintaining an assembly 110, 410 that includes the one or more chemical warming agents 630 adjacent a first cold-sensitive device 270; and removing a single-piece layer 121 so as to (create or otherwise) establish the first (effective) oxygen ingress area A1 of the one or more chemical warming agents 630 and thereby to activate the one or more chemical warming agents 630 at the corresponding first heat emission rate R1, wherein the first oxygen barrier includes the single-piece layer 121.

12. The method of any of the above METHOD CLAUSES, wherein the opening the first oxygen barrier of the first exclusion structure comprises:

maintaining an assembly 110, 410 that includes the one or more chemical warming agents 630 adjacent a first cold-sensitive device 270 while removing a single-piece layer 121 so as to (create or otherwise) establish the first (effective) oxygen ingress area A1 of the one or more chemical warming agents 630 and thereby to activate the one or more chemical warming agents 630 at the corresponding first heat emission rate R1, wherein the first oxygen barrier includes the single-piece layer 121.

13. The method of any of the above METHOD CLAUSES, wherein the configuring the second oxygen barrier of the second exclusion structure essentially consists of:

maintaining an assembly 110, 410 that includes the one or more chemical warming agents 630 adjacent a first cold-sensitive device 270; and removing a single-piece layer 122 so as to (create or otherwise) establish the first (effective) oxygen ingress area A2 of the one or more chemical warming agents 630 and thereby to activate the one or more chemical warming agents 630 at the corresponding second heat emission rate R2, wherein the second oxygen barrier includes the single-piece layer 122.

14. The method of any of the above METHOD CLAUSES, wherein the configuring the second oxygen barrier of the second exclusion structure comprises:

maintaining an assembly 110, 410 that includes the one or more chemical warming agents 630 adjacent a first cold-sensitive device 270 while removing a single-piece layer 122 so as to (create or otherwise) establish the first (effective) oxygen ingress area A2 of the one or more chemical warming agents 630 and thereby to activate the one or more chemical warming agents 630 at the corresponding second heat emission rate R2, wherein the second oxygen barrier includes the single-piece layer 122.

15. The method of any of the above METHOD CLAUSES, wherein the opening the first oxygen barrier of the first exclusion structure comprises:

allowing air to flow through several ports 141 of an infrared-reflective film layer 125 to the one or more chemical warming agents 630 by the opening the first oxygen barrier, whereby at least 25% of infrared energy thereby emitted by the activation of the one or more chemical warming agents 630 is reflected (e.g. back toward or through the one or more chemical warming agents 630).

16. The method of any of the above METHOD CLAUSES, wherein the opening the first oxygen barrier of the first exclusion structure comprises:

allowing air to flow through more than a dozen ports 141 of a film layer 125 to the one or more chemical warming agents 630 by the opening the first oxygen barrier.

17. The method of any of the above METHOD CLAUSES, wherein the opening the first oxygen barrier of the first exclusion structure comprises:

allowing air to flow through several corresponding ports 141 to the one or more chemical warming agents 630 by the opening the first oxygen barrier, wherein the one or more corresponding ports 141 each have an area 145A within an order of magnitude of 10 square millimeters.

18. The method of any of the above METHOD CLAUSES, wherein the opening the first oxygen barrier of the first exclusion structure comprises:

allowing air to flow through a corresponding plurality of ports 141 to the one or more chemical warming agents 630 by the opening the first oxygen barrier, wherein the a corresponding plurality of ports 141 has an (effective) aggregate area 145A greater than 30 square millimeters.

19. The method of any of the above METHOD CLAUSES, wherein the opening the first oxygen barrier of the first exclusion structure comprises:

allowing air to flow through a corresponding plurality of ports 141 to the one or more chemical warming agents 630 by the opening the first oxygen barrier, wherein the a corresponding plurality of ports 141 has an (effective) aggregate area 145A less than 300 square millimeters.

20. The method of any of the above METHOD CLAUSES, wherein the configuring the second oxygen barrier of the second exclusion structure comprises:

allowing air to flow through several corresponding ports 142 to the one or more chemical warming agents 630 by the opening the second oxygen barrier, wherein the one or more corresponding ports 142 each have an area 145B within an order of magnitude of 10 square millimeters.

21. The method of any of the above METHOD CLAUSES, wherein the configuring the second oxygen barrier of the second exclusion structure comprises:

allowing air to flow through a corresponding plurality of ports 142 to the one or more chemical warming agents 630 by the opening the second oxygen barrier, wherein the a corresponding plurality of ports 142 has an (effective) aggregate area 145B greater than 30 square millimeters.

22. The method of any of the above METHOD CLAUSES, wherein the configuring the second oxygen barrier of the second exclusion structure comprises:

allowing air to flow through a corresponding plurality of ports 142 to the one or more chemical warming agents 630 by the opening the second oxygen barrier, wherein the a corresponding plurality of ports 142 has an (effective) aggregate area 145B less than 300 square millimeters.

23. The method of any of the above METHOD CLAUSES, wherein the configuring the second oxygen barrier of the second exclusion structure comprises:

allowing air to flow through several ports 142 of an infrared-reflective film layer 125 to the one or more chemical warming agents 630 by the opening the first oxygen barrier, whereby at least 25% of infrared energy thereby emitted by the activation of the one or more chemical warming agents 630 is reflected (e.g. back toward or through the one or more chemical warming agents 630).

24. The method of any of the above METHOD CLAUSES, wherein the configuring the second oxygen barrier of the second exclusion structure comprises:

allowing air to flow through more than a dozen ports 142 of a film layer 125 to the one or more chemical warming agents 630 by the configuring the first oxygen barrier.

25. The method of any of the above METHOD CLAUSES, comprising:

affixing a restickable adhesive 644 (i.e. one that comprises at least some microstructures that effectively reduce an amount of surface area in contact between the adhesive 644 and an adhered substrate by more than 0.1%) between a first cold-sensitive device 270, 370, 670 and the assembly that includes the one or more chemical warming agents 630, wherein the restickable adhesive 644 is one of the one or more positioning elements.

26. The method of any of the above METHOD CLAUSES, wherein an opening, encasement, or other prescribed manual action (by user 201, e.g.) effectively triggers a selective transition to the adjusted heat emission rate R2 and thereby causes the device 270, 370, 670 to be warmed by the one or more chemical warming agents 630 in a frigid environment 500.

27. The method of any of the above METHOD CLAUSES, wherein an opening, encasement, or other prescribed manual action (by user 201, e.g.) effectively triggers a selective transition to the adjusted heat emission rate R2 and thereby causes the device 270, 370, 670 to be (kept warm or otherwise) warmed in a manner related to the second heat emission rate R2.

28. The method of any of the above METHOD CLAUSES, comprising:
configuring at least one of the one or more positioning elements to position the one or more chemical warming agents 630 within a chamber 447 adjacent a first cold-sensitive device 270, 370, 670 before configuring the second oxygen barrier of the second exclusion structure.

29. The method of any of the above METHOD CLAUSES, comprising:
configuring at least one of the one or more positioning elements to position the one or more chemical warming agents 630 adjacent a first cold-sensitive device 270, 370, 670 before configuring the second oxygen barrier of the second exclusion structure.

30. The method of any of the above METHOD CLAUSES, comprising:
configuring at least one of the one or more positioning elements to position the one or more chemical warming agents 630 adjacent a first cold-sensitive device 270, 370, 670 while configuring the second oxygen barrier of the second exclusion structure.

31. The method of any of the above METHOD CLAUSES, comprising:
configuring at least one of the one or more positioning elements to position the one or more chemical warming agents 630 adjacent a first cold-sensitive device 270, 370, 670 after configuring the second oxygen barrier of the second exclusion structure.

32. The method of any of the above METHOD CLAUSES, wherein the first heat emission rate R1 peaks within five minutes after the first oxygen barrier of the first exclusion structure and declines steadily thereafter for five minutes before the second oxygen barrier of the second exclusion structure is configured so as to establish the second oxygen ingress area A2.

33. The method of any of the above METHOD CLAUSES, wherein the configuring the second oxygen barrier of the second exclusion structure is performed after the opening the first oxygen barrier of the first exclusion structure so as to establish the first oxygen ingress area A1 (as area 145A, e.g.) of the one or more chemical warming agents 630 and thereby to initiate the activation of the one or more chemical warming agents 630 at the corresponding first heat emission rate R1 is complete.

34. The method of any of the above METHOD CLAUSES, wherein the opening the first oxygen barrier of the first exclusion structure comprises:
removing one or more layers 121, 122 (comprising an oxygen-impermeable envelope 615, e.g.) from an assembly 110, 410 that includes the one or more chemical warming agents 630.

35. The method of any of the above METHOD CLAUSES, wherein the opening the first oxygen barrier of the first exclusion structure comprises:
removing one or more layers 121, 122 from a single side 494B of an assembly 110, 410 that includes the one or more chemical warming agents 630.

36. The method of any of the above METHOD CLAUSES, wherein the obtaining one or more chemical warming agents 630 comprises:
receiving an assembly 110, 410 that includes the one or more chemical warming agents 630.

37. The method of any of the above METHOD CLAUSES, wherein a prescribed manual opening of a partial layer 121, 521 (covering less than 80% of a side 494A-B, e.g.) effectively triggers the first heat emission at rate R1.

38. The method of any of the above METHOD CLAUSES, wherein the activation of the one or more chemical warming agents at the corresponding first heat emission rate R1 occurs swiftly (i.e. within 30 seconds) upon the first oxygen barrier of the first exclusion structure being opened.

39. The method of any of the above METHOD CLAUSES, wherein a total amount 131 of the one or more chemical warming agents 630 in an assembly 110, 410 thereof is within an order of magnitude of 35 grams.

40. The method of any of the above METHOD CLAUSES, wherein a total amount 131 of the one or more chemical warming agents 630 in an assembly 110, 410 thereof is greater than 5 grams.

41. The method of any of the above METHOD CLAUSES, wherein a total amount 131 of the one or more chemical warming agents 630 in an assembly 110, 410 thereof is greater than 25 grams.

42. The method of any of the above METHOD CLAUSES, wherein a total amount 131 of the one or more chemical warming agents 630 in an assembly 110, 410 thereof is less than 120 grams.

43. The method of any of the above METHOD CLAUSES, wherein a total amount 131 of the one or more chemical warming agents 630 in an assembly 110, 410 thereof is less than 200 grams.

44. The method of any of the above METHOD CLAUSES, wherein the one or more chemical warming agents 630 in an assembly 110, 410 thereof comprise a mixture 130 of at least 1% by weight of activated carbon 133 and at least 0.5% by weight of vermiculite 135.

45. The method of any of the above METHOD CLAUSES, wherein the one or more chemical warming agents 630 in an assembly 110, 410 thereof comprise a mixture 130 of at least 5% by weight of combustible organic matter 132 (dry wood fiber, e.g.) and at least 1% by weight of activated carbon 133.

46. The method of any of the above METHOD CLAUSES, wherein the one or more chemical warming agents 630 in an assembly 110, 410 thereof comprise a mixture 130 of at least 5% by weight of combustible organic matter 132 (dry wood fiber, e.g.) and at least 0.5% by weight of vermiculite 135.

47. The method of any of the above METHOD CLAUSES, wherein the one or more chemical warming agents 630 in an assembly 110, 410 thereof comprise a mixture 130 of at least 5% by weight of combustible organic matter 132 (dry wood fiber, e.g.) and at least 0.5% by weight of iron 136.

48. The method of any of the above METHOD CLAUSES, wherein the one or more chemical warming agents 630 in an assembly 110, 410 thereof comprise a mixture 130 of at least 1% by weight of activated carbon 133 and at least 0.5% by weight of iron 136.

49. The method of any of the above METHOD CLAUSES, wherein the one or more chemical warming agents 630 in an assembly 110, 410 thereof comprise a mixture 130 of at least 0.5% by weight of vermiculite 135 and at least 0.5% by weight of iron 136.

50. The method of any of the above METHOD CLAUSES, wherein the one or more chemical warming agents 630 in an assembly 110, 410 thereof comprise a mixture 130 of at least 5% by weight of combustible organic matter 132 (dry wood fiber, e.g.) and at least 0.5% by weight of salt 138.

51. The method of any of the above METHOD CLAUSES, wherein the one or more chemical warming agents 630 in an assembly 110, 410 thereof comprise a mixture 130 of at least 1% by weight of activated carbon 133 and at least 0.5% by weight of salt 138.

52. The method of any of the above METHOD CLAUSES, wherein the one or more chemical warming agents 630 in an assembly 110, 410 thereof comprise a mixture 130 of at least 0.5% by weight of vermiculite 135 and at least 0.5% by weight of salt 138.

53. The method of any of the above METHOD CLAUSES, wherein the one or more chemical warming agents 630 in an assembly 110, 410 thereof comprise a mixture 130 of at least 0.5% by weight of iron 136 and at least 0.5% by weight of salt 138.

54. The method of any of the above METHOD CLAUSES, wherein the configuring the second oxygen barrier of the second exclusion structure comprises:
creating one or more openable ports 142, 342 having a nominal (aggregate or other) second (effective) oxygen ingress area A2 (as area 145B, e.g.) of the one or more chemical warming agents 630 and thereby modifying the activation of the one or more chemical warming agents 630 to a corresponding second heat emission rate R2 (as rate 195B, e.g.) within one hour of the second oxygen barrier being configured.

55. The method of any of the above METHOD CLAUSES, wherein the configuring the second oxygen barrier comprises:
configuring a chamber 447 adjacent the device 270, 370, 670 (by removing a cover 348, e.g.); and
causing an assembly 110, 410 that includes the one or more chemical warming agents 630 to extend into the chamber 447.

56. The method of any of the above METHOD CLAUSES, wherein the second heat emission rate R2 is greater than the first heat emission rate R1.

57. The method of any of the above METHOD CLAUSES, wherein the second heat emission rate R2 differs from the first heat emission rate R1 by more than 10%.

58. The method of any of the above METHOD CLAUSES, wherein the second heat emission rate R2 differs from the first heat emission rate R1 by more than 50%.

59. The method of any of the above METHOD CLAUSES, comprising:
configuring at least one of the one or more positioning elements to position the one or more chemical warming agents 630 within a chamber 447 adjacent a first cold-sensitive device 270, 370, 670 before configuring the second oxygen barrier of the second exclusion structure.

60. The method of any of the above METHOD CLAUSES, comprising:
configuring at least one of the one or more positioning elements to position the one or more chemical warming agents 630 adjacent a first cold-sensitive device 270, 370, 670 before configuring the second oxygen barrier of the second exclusion structure.

61. The method of any of the above METHOD CLAUSES, comprising:
configuring at least one of the one or more positioning elements to position the one or more chemical warming agents 630 adjacent a first cold-sensitive device 270, 370, 670 while configuring the second oxygen barrier of the second exclusion structure.

62. The method of any of the above METHOD CLAUSES, comprising:
configuring at least one of the one or more positioning elements to position the one or more chemical warming agents 630 adjacent a first cold-sensitive device 270, 370, 670 after configuring the second oxygen barrier of the second exclusion structure.

63. The method of any of the above METHOD CLAUSES, wherein the first heat emission rate R1 peaks within five minutes after the first oxygen barrier of the first exclusion structure and declines steadily thereafter for five minutes before the second oxygen barrier of the second exclusion structure is configured so as to establish the second oxygen ingress area A2.

64. The method of any of the above METHOD CLAUSES, wherein the configuring the second oxygen barrier of the second exclusion structure is performed after the opening the first oxygen barrier of the first exclusion structure so as to establish the first oxygen ingress area A1 (as area 145A, e.g.) of the one or more chemical warming agents 630 and thereby to initiate the activation of the one or more chemical warming agents 630 at the corresponding first heat emission rate R1 is complete.

65. (Independent) An air-activated device warming system, comprising:
one or more chemical warming agents 630 (having within an order of magnitude of 35 grams of a mixture 130 in an assembly 110 thereof, e.g.);
a first oxygen barrier (an airtight layer 121, 621, e.g.) of a first exclusion structure configured to be opened so as to establish a (vapor barrier including one or more openable ports 621 or otherwise having an aggregate or other nominal) first oxygen ingress area A1 (as area 145A, e.g.) of the one or more chemical warming agents 630 and thereby to initiate an activation of the one or more chemical warming agents 630 at a corresponding first heat emission rate R1, wherein A1>1 square millimeter and wherein R1 reaches within an order of magnitude of 100-1000 calories per second (dependent) upon the first oxygen barrier being opened; and
a second oxygen barrier (a cover 348 or other closable structure, e.g.) of a second exclusion structure (a cover 348 or other container, e.g.) configured so as to establish one or more openable ports 142, 342 having an (aggregated second effective) oxygen ingress area A2 (as an overall ingress area 145B, e.g.) of the one or more chemical warming agents 630 and thereby to modify the activation of the one or more chemical warming agents 630 to a corresponding second heat emission rate R2 (as rate 195B, e.g.), wherein the second oxygen ingress area A2 differs from the first oxygen ingress area A1 by more than 1%.

66. The system of any of the above SYSTEM CLAUSES, wherein the first exclusion structure comprises an envelope 615.

67. The system of any of the above SYSTEM CLAUSES, wherein the second exclusion structure includes a coating or other infrared-reflective layer 429.

68. The system of any of the above SYSTEM CLAUSES, comprising:
an assembly 110, 410 that contains the one or more chemical warming agents 630 having a primary side 494A thereof that is adjacent a first cold-sensitive device 270, 370, 670 and a distal side thereof that is not adjacent the cold-sensitive device 270, 370, 670, wherein the primary side 494A is more than 1% smaller than the distal side 494B.

69. The system of any of the above SYSTEM CLAUSES, comprising:
a cold-sensitive device 270, 370, 670 configured to be warmed by the activation of the one or more chemical warming agents 630, wherein the cold-sensitive device is rendered operative in a frigid environment by an activation of the one or more chemical warming agents.

70. The system of any of the above SYSTEM CLAUSES, wherein the second exclusion structure (comprising a case 360 or other assembly 110, 410 that contains the one or more chemical warming agents 630, e.g.) has (one or more air containment chambers 447 with) an (initial) air volume 367 greater than 20 milliliters.

71. The system of any of the above SYSTEM CLAUSES, wherein the second exclusion structure (comprising a case 360 or other assembly 110, 410 that contains the one or more chemical warming agents 630, e.g.) has (one or more air containment chambers 447 with) an (initial) air volume 367 less than 80 milliliters.

72. The system of any of the above SYSTEM CLAUSES, comprising:
an entirety of the first exclusion structure.

73. The system of any of the above SYSTEM CLAUSES, comprising:
an entirety of the second exclusion structure.

74. The system of any of the above SYSTEM CLAUSES, wherein the second exclusion structure at least partly comprises a phone case 360.

75. The system of any of the above SYSTEM CLAUSES, wherein the second exclusion structure at least partly comprises a removable cover 348.

76. The system of any of the above SYSTEM CLAUSES, wherein the second exclusion structure at least partly comprises a replaceable cover 348.

77. The system of any of the above SYSTEM CLAUSES, configured to be made or used (or both) according to any of the above METHOD CLAUSES.

While various system, method, article of manufacture, or other embodiments or aspects have been disclosed above, also, other combinations of embodiments or aspects will be apparent to those skilled in the art in view of the above disclosure. The various embodiments and aspects disclosed above are for purposes of illustration and are not intended to be limiting, with the true scope and spirit being indicated in the final claim set that follows.

What is claimed is:

1. A device-warming method comprising:
obtaining one or more oxygen-activated chemical warming agents;
opening a first oxygen barrier of a first exclusion structure so as to establish a first oxygen ingress area A1 of said one or more oxygen-activated chemical warming agents and thereby to initiate an activation of said one or more oxygen-activated chemical warming agents at a corresponding first heat emission rate R1, wherein A1>1 square millimeter and wherein R1 reaches within an order of magnitude of 100-1000 calories per second upon said first oxygen barrier being opened;
configuring a second oxygen barrier of a second exclusion structure so as to establish a second oxygen ingress area A2 of said one or more oxygen-activated chemical warming agents and thereby to modify said activation of said one or more oxygen-activated chemical warming agents to a corresponding second heat emission rate R2, wherein said second oxygen ingress area A2 differs from said first oxygen ingress area A1 by more than 5% so as to allow a cold-sensitive device to be warmed by said one or more oxygen-activated chemical warming agents; and
affixing a restickable adhesive between said cold-sensitive device and an assembly that includes said one or more oxygen-activated chemical warming agents.

2. The device-warming method of claim 1, wherein said configuring said second oxygen barrier of said second exclusion structure comprises:
allowing air to flow through several ports of an infrared-reflective film layer to said one or more oxygen-activated chemical warming agents by said opening said first oxygen barrier, whereby at least 25% of infrared energy thereby emitted by said activation of said one or more oxygen-activated chemical warming agents is reflected.

3. A device-warming method comprising:
obtaining one or more oxygen-activated chemical warming agents;
opening a first oxygen barrier of a first exclusion structure so as to establish a first oxygen ingress area A1 of said one or more oxygen-activated chemical warming agents and thereby to initiate an activation of said one or more oxygen-activated chemical warming agents at a corresponding first heat emission rate R1, wherein A1>1 square millimeter and wherein R1 reaches within an order of magnitude of 100-1000 calories per second upon said first oxygen barrier being opened;
configuring a second oxygen barrier of a second exclusion structure so as to establish a second oxygen ingress area A2 of said one or more oxygen-activated chemical warming agents and thereby to modify said activation of said one or more oxygen-activated chemical warming agents to a corresponding second heat emission rate R2, wherein said second oxygen ingress area A2 differs from said first oxygen ingress area A1 by more than 5% so as to allow a cold-sensitive device to be warmed by said one or more oxygen-activated chemical warming agents; and
configuring one or more positioning elements to position said one or more oxygen-activated chemical warming agents within a chamber adjacent said cold-sensitive device.

4. A device-warming method comprising:
obtaining one or more oxygen-activated chemical warming agents;
opening a first oxygen barrier of a first exclusion structure so as to establish a first oxygen ingress area A1 of said one or more oxygen-activated chemical warming agents and thereby to initiate an activation of said one or more oxygen-activated chemical warming agents at a corresponding first heat emission rate R1, wherein A1>1 square millimeter and wherein R1 reaches within an order of magnitude of 100-1000 calories per second upon said first oxygen barrier being opened;
configuring a second oxygen barrier of a second exclusion structure so as to establish a second oxygen ingress area A2 of said one or more oxygen-activated chemical warming agents and thereby to modify said activation of said one or more oxygen-activated chemical warming agents to a corresponding second heat emission rate R2, wherein said second oxygen ingress area A2 differs from said first oxygen ingress area A1 by more than 5% so as to allow a first cold-sensitive device to be warmed by said one or more oxygen-activated chemical warming agents; and configuring at least one of one or more positioning elements to position said one or more oxygen-activated chemical warming agents adjacent said first cold-sensitive device after configuring said second oxygen barrier of said second exclusion structure, wherein said second heat emission rate R2 differs from said first heat emission rate R1 by more than 10%.

5. The device-warming method of claim 1 wherein said configuring said second oxygen barrier of said second exclusion structure is performed after said opening said first oxygen barrier of said first exclusion structure so as to establish said first oxygen ingress area A1 of said one or more oxygen-activated chemical warming agents and thereby to initiate said activation of said one or more oxygen-activated chemical warming agents at said corresponding first heat emission rate R1 is complete.

6. An air-activated device warming system, comprising:
one or more oxygen-activated chemical warming agents;
a first oxygen barrier of a first exclusion structure configured to be opened so as to establish a first oxygen ingress area A1 of said one or more oxygen-activated chemical warming agents and thereby to initiate an activation of said one or more oxygen-activated chemical warming agents at a corresponding first heat emission rate R1, wherein A1>1 square millimeter and wherein R1 reaches within an order of magnitude of 100-1000 calories per second upon said first oxygen barrier being opened;
a second oxygen barrier of a second exclusion structure configured so as to establish a second oxygen ingress area A2 of said one or more oxygen-activated chemical warming agents and thereby to modify said activation of said one or more oxygen-activated chemical warming agents to a corresponding second heat emission rate R2, wherein said second oxygen ingress area A2 differs from said first oxygen ingress area A1 by more than 5% so as to allow a cold-sensitive device to be warmed by said one or more oxygen-activated chemical warming agents; and
one or more positioning elements configured to position said one or more oxygen-activated chemical warming agents within a chamber adjacent said cold-sensitive device.

7. The device-warming system of claim 6, wherein said one or more oxygen-activated chemical warming agents comprise a mixture of at least 1% by weight of activated carbon, at least 5% by weight of combustible organic matter, at least 0.5% by weight of salt, and at least 0.5% by weight of vermiculite.

8. The device-warming system of claim 6, wherein an assembly that contains the one or more oxygen-activated chemical warming agents has a primary side thereof that is adjacent said cold-sensitive device and a distal side thereof that is not adjacent said cold-sensitive device, wherein said primary side is more than 1% smaller than said distal side.

9. The device-warming method of claim 3 wherein said activation of said one or more oxygen-activated chemical warming agents to said corresponding second heat emission rate R2 occurs within one hour of beginning said configuring said second oxygen barrier of said second exclusion structure.

10. The device-warming method of claim 3 wherein said one or more oxygen-activated chemical warming agents comprise a mixture of at least 1% by weight of activated carbon, at least 0.5% by weight of vermiculite, at least 0.5% by weight of iron, and at least 0.5% by weight of salt.

11. The device-warming method of claim 3 wherein said second oxygen ingress area A2 differs from said first oxygen ingress area A1 by more than 25%.

12. The device-warming method of claim 1 comprising:
configuring an assembly that contains said one or more oxygen-activated chemical warming agents so that a total amount of said one or more oxygen-activated chemical warming agents in said assembly is within an order of magnitude of 35 grams.

13. The device-warming method of claim 1 wherein said activation of said one or more oxygen-activated chemical warming agents to said corresponding second heat emission rate R2 occurs within one hour of beginning said configuring said second oxygen barrier of said second exclusion structure.

14. The device-warming method of claim 4 wherein said one or more oxygen-activated chemical warming agents comprise a mixture of at least 1% by weight of activated carbon, at least 0.5% by weight of vermiculite, at least 0.5% by weight of iron, and at least 0.5% by weight of salt.

15. The device-warming method of claim 4 wherein said second oxygen ingress area A2 differs from said first oxygen ingress area A1 by more than 25%.

16. The device-warming method of claim 4 comprising:
configuring an assembly that contains said one or more oxygen-activated chemical warming agents so that a total amount of said one or more oxygen-activated chemical warming agents in said assembly is within an order of magnitude of 35 grams.

17. An air-activated device warming system, comprising:
one or more oxygen-activated chemical warming agents;
a first oxygen barrier of a first exclusion structure configured to be opened so as to establish a first oxygen ingress area A1 of said one or more oxygen-activated chemical warming agents and thereby to initiate an activation of said one or more oxygen-activated chemical warming agents at a corresponding first heat emission rate R1, wherein A1>1 square millimeter and wherein R1 reaches within an order of magnitude of 100-1000 calories per second upon said first oxygen barrier being opened;
a second oxygen barrier of a second exclusion structure configured so as to establish a second oxygen ingress area A2 of said one or more oxygen-activated chemical warming agents and thereby to modify said activation of said one or more oxygen-activated chemical warming agents to a corresponding second heat emission rate R2, wherein said second oxygen ingress area A2 differs from said first oxygen ingress area A1 by more than 5% so as to allow a cold-sensitive device to be warmed by said one or more oxygen-activated chemical warming agents; and
a restickable adhesive affixed between said cold-sensitive device and an assembly that includes said one or more oxygen-activated chemical warming agents wherein one or more positioning elements that include said restickable adhesive are configured to position said one or more oxygen-activated chemical warming agents within a chamber adjacent said cold-sensitive device.

18. The device-warming system of claim 17 wherein said one or more oxygen-activated chemical warming agents comprise a mixture of at least 1% by weight of activated carbon, at least 5% by weight of combustible organic matter, at least 0.5% by weight of salt, and at least 0.5% by weight of vermiculite.

19. The device-warming system of claim 17 wherein an assembly that contains the one or more oxygen-activated chemical warming agents has a primary side thereof that is adjacent said cold-sensitive device and a distal side thereof that is not adjacent said cold-sensitive device, wherein said primary side is more than 1% smaller than said distal side.

* * * * *